United States Patent
Gross et al.

(10) Patent No.: US 9,586,460 B2
(45) Date of Patent: Mar. 7, 2017

(54) AIR PURIFICATION SYSTEM FOR VEHICLES

(75) Inventors: Bernd Gross, Langenfeld (DE);
Hans-Georg Werner, Langenfeld (DE);
Joshua Hesterberg, Mettmann (DE);
Man Loong Leong, Pahang (MY)

(73) Assignee: Johnson Controls Technology Company, Holland, MI (US)

( * ) Notice: Subject to any disclaimer, the term of this patent is extended or adjusted under 35 U.S.C. 154(b) by 1543 days.

(21) Appl. No.: 13/127,919

(22) PCT Filed: Nov. 5, 2009

(86) PCT No.: PCT/EP2009/007939
§ 371 (c)(1),
(2), (4) Date: Jul. 18, 2011

(87) PCT Pub. No.: WO2010/052001
PCT Pub. Date: May 14, 2010

(65) Prior Publication Data
US 2012/0128539 A1    May 24, 2012

(30) Foreign Application Priority Data
Nov. 5, 2008  (DE) .................. 10 2008 055 988

(51) Int. Cl.
*B60H 3/00* (2006.01)
*A61L 9/20* (2006.01)
(Continued)

(52) U.S. Cl.
CPC ............ *B60H 3/0078* (2013.01); *A61L 9/205* (2013.01); *F24F 3/166* (2013.01); *B60H 2003/0675* (2013.01); *F24F 2003/1667* (2013.01)

(58) Field of Classification Search
CPC ......... B60H 3/0078; A61L 9/205; F24F 3/166
(Continued)

(56) References Cited

U.S. PATENT DOCUMENTS 4,658,707 A * 4/1987 Hawkins ............. B60H 3/0608
454/140
5,001,905 A * 3/1991 Miyazaki ........... B60H 1/00371
454/161
(Continued)

FOREIGN PATENT DOCUMENTS

CN      2621046 Y    6/2004
CN      2660374 Y    12/2004
(Continued)

OTHER PUBLICATIONS

Japanese Office Action dated Dec. 9, 2013.
(Continued)

*Primary Examiner* — Regina M Yoo
(74) *Attorney, Agent, or Firm* — Fletcher Yoder, P.C.

(57) ABSTRACT

An air purification device for a vehicle comprises an air inlet, an air outlet, and an air conduction volume between the air inlet and the air outlet. At least one reaction surface element is provided in the air conduction volume. At least one light source for ultraviolet light is arranged in the air conduction volume. A surface of the at least one reaction surface element comprises a catalytic material, and the at least on reaction surface element is arranged substantially in the entire air conduction volume or occupies at least 50% of the inner surface of the air purification device. The air purification device comprises a base element and a cover element. The at least one reaction surface element is integrally connected to the base element or to the cover element and comprises surface-coated rod-shaped elements protruding into the air conduction volume.

20 Claims, 7 Drawing Sheets

(51) Int. Cl.
  *F24F 3/16* (2006.01)
  *B60H 3/06* (2006.01)

(58) Field of Classification Search
  USPC .................................................. 422/120, 122
  See application file for complete search history.

(56) References Cited

U.S. PATENT DOCUMENTS

| | | | | |
|---|---|---|---|---|
| 5,032,241 | A * | 7/1991 | Robertson et al. | 204/157.15 |
| 5,865,959 | A * | 2/1999 | Meinzer et al. | 204/157.3 |
| 5,919,422 | A | 7/1999 | Yamanaka et al. | |
| 6,094,767 | A * | 8/2000 | Iimura | 15/105 |
| 6,239,442 | B1 * | 5/2001 | Iimura | 250/504 R |
| 6,620,385 | B2 * | 9/2003 | Fujii | 422/186.3 |
| 6,678,425 | B1 * | 1/2004 | Flores et al. | 382/289 |
| 7,820,100 | B2 * | 10/2010 | Garfield et al. | 422/1 |
| 8,328,917 | B2 * | 12/2012 | Garfield et al. | 96/224 |
| 2007/0119699 | A1 * | 5/2007 | Chambers et al. | 204/176 |
| 2007/0144351 | A1 * | 6/2007 | Taira | A61L 9/205 96/223 |
| 2008/0050272 | A1 * | 2/2008 | Carey | 422/4 |
| 2008/0152548 | A1 * | 6/2008 | Clark et al. | 422/121 |
| 2009/0068058 | A1 * | 3/2009 | Kim | B60H 3/0014 422/4 |
| 2009/0123343 | A1 * | 5/2009 | Kwiatkowski | 422/121 |
| 2010/0254868 | A1 * | 10/2010 | Obee et al. | 423/210 |

FOREIGN PATENT DOCUMENTS

| | | | | |
|---|---|---|---|---|
| CN | 2712359 | Y | 7/2005 | |
| DE | 19732304 | A1 | 1/1999 | |
| DE | 19853981 | A1 | 7/1999 | |
| DE | 19906113 | A1 | 8/2000 | |
| DE | 19961617 | A1 | 7/2001 | |
| DE | 10124662 | A1 | 11/2002 | |
| JP | 63-80833 | | 11/1988 | |
| JP | 2002036971 | | 2/2002 | |
| JP | 2002045416 | A * | 2/2002 | A61L 9/00 |
| JP | 2005-007306 | | 1/2005 | |
| JP | 2007051520 | A * | 3/2007 | E04H 4/12 |
| WO | 02078754 | A1 | 10/2002 | |
| WO | WO 2009047668 | A3 * | 6/2009 | A61L 9/20 |

OTHER PUBLICATIONS

Japanese Examination Report dated Jan. 8, 2013.
DE 10 2008 055 987.3-16 Office Action dated May 6, 2009; 3 pgs.
PCT/EP2009/007939 International Preliminary Report & Written Opinion; May 10, 2011; 7 pgs.
Chinese Examination Report dated Dec. 26, 2012.
Chinese Office Action dated Jul. 12, 2013.
Perry, "Perry's Chemical Engineer's Handbook," Aug. 1993, 20th article, pp. 169-178, vol. II, sixth edition.

* cited by examiner

AIR PURIFICATION SYSTEM FOR VEHICLES

CROSS REFERENCE TO RELATED APPLICATIONS

This application claims priority from and the benefit of PCT Application No. PCT/EP2009/007939, filed on Nov. 5, 2009, and German Patent DE 10 2008 055 988.1, filed on Nov. 5, 2008; all entitled "Air Purification System for Vehicles", which are herein incorporated by reference.

BACKGROUND

The present invention relates to an air purification system, in particular for vehicles or airplanes or other means of transport.

Particularly for the interior of a vehicle, it is of great importance to generate clean air, in particular air that is substantially free of germs and contains no organic pollutants, especially to ensure the well-being of the vehicle occupants and thus also to ensure a high level of safety of the vehicle. There is therefore a great economic interest in purifying the air inside a vehicle inexpensively and effectively and, in particular, using a compact device that can be produced at low cost and can be run with relatively little power consumption. Known devices for purifying air include ozone generators, filter systems, air ionizers and the like. Filter systems are in principle suitable only for separating fairly large particulate air components (dust, pollen, microorganisms). They have the disadvantage that the filters have to be regularly replaced or regenerated.

In catalytic air purification by means of titanium dioxide, hydroxyl radicals $OH^-$ and super oxides $O_2^-$ are formed by a photochemical reaction. All organic trace element molecules or air pollutant molecules are completely oxidized in the presence of atmospheric oxygen, i.e. an as it were cold combustion reaction of atmospheric oxygen takes place with formation of carbon dioxide ($CO_2$) and water ($H_2O$) and, if appropriate, other non-toxic products. A decomposition/conversion of the pollutants takes place at the same time.

Disadvantages of known methods of photocatalytic air purification lie in their low efficiency, particularly on account of a small reaction surface in the reaction space, of the resulting need for a longer dwell time in the reaction space, of a less complete reaction and the discharge of (most of the) primary products with the air stream.

SUMMARY

The object of the invention was therefore to make available an air purification system for vehicles which, despite a very small installation space, permits maximum air purification. In particular, the invention is intended to allow the air purification system or an air purification device to be made so compact that installation in a vehicle seat is possible.

The object is achieved by means of an air purification system or an air purification device, in particular for a vehicle, the air purification device having an air inlet, an air outlet, and an air conduction volume between air inlet and air outlet, at least one reaction surface element being provided in the air conduction volume, wherein at least one light source for ultraviolet light is arranged in the air conduction volume, wherein the surface of the reaction surface element has a catalytic material, and wherein the reaction surface element is arranged substantially in the entire air conduction volume, or wherein the reaction surface element occupies at least 50%, preferably at least 60%, particularly preferably at least 70%, of the inner surface of the air purification device.

According to the invention, it is thus advantageously possible to produce an air purification device in which a maximum reaction surface is permitted within a small installation space, especially by means of a particular configuration of an air channel, and in which highly effective and in particular photocatalytic purification is permitted by a particular arrangement of one or more light sources and/or by a particular number of light sources.

With the air purification system according to the invention or the air purification device according to the invention, it is advantageously possible, according to the invention, for the air inside a vehicle to be purified to a high degree, in particular to be freed of unpleasant odors, within a relatively short time, for example within 30 minutes, and for germs or bacteria or viruses to be effectively killed off. Provision is also made, according to the invention, that purified air preferably first reaches those places in the vehicle interior where there is a relatively high probability of a passenger inhaling the air. Such places in the vehicle interior are, for example, basically the entire area underneath the roof liner of the vehicle, because the heads of the vehicle occupants are preferably situated in this spatial area.

According to the invention, the reaction surface element is arranged substantially in the entire air conduction volume of the air purification device. For example, the reaction surface element substantially completely fills the air conduction volume (for example in the form of a filler material, which is surface-coated) or extends at least over the entire area of the air conduction volume (for example in the form of a lattice or net or wire mesh or surface-coated fiber element, which extends over the entire area of the air conduction volume). According to the invention, it is particularly preferable in this connection if the reaction surface element is arranged in at least 60% of the air conduction volume, preferably in at least 80% of the air conduction volume or also in at least 90% of the air conduction volume.

According to the invention, provision is preferably made that the catalytic material contains titanium dioxide. A particularly good purifying action can be achieved in this way. The purifying action can be further increased if the air purification device has a further air conduction volume (separate from or upstream of the air conduction volume), the further air conduction volume having a zeolite material and/or a silver substrate material as a further catalytic material, i.e. without the presence of titanium dioxide as catalytic material and also without lighting with a UV-A light source in the further air conduction volume.

Furthermore, according to the invention, it is also preferred that the reaction surface element has a surface-coated carrier element, in particular a lattice or a wire mesh or a fiber material, preferably a zeolite material and/or a silver substrate material. In this way it is possible to ensure a particularly well-defined spatial arrangement of the material of the surface coating, according to the invention in particular a material containing titanium dioxide, which arrangement also remains substantially unchanged during the lifetime of the air purification device. In this way it is also possible to achieve particularly well-defined and efficient lighting of the surface coating by the light source or the light sources. According to the invention, it is also possible in this way for the flow resistance of the air flowing through the air purification device to be kept relatively low. Moreover, by means of the defined arrangement of the surface-coated carrier element, it is also advantageously possible for the flow resistance to remain substantially the same, or to change in a relatively well-defined manner, during the period of use of the air purification device.

Moreover, it is likewise preferable that the reaction surface element is designed as surface-coated bulk material, particularly in the form of glass tube sections and/or in the form of glass balls. It is thus possible in a simple way to achieve a particularly large surface area of the surface-active substance, i.e. of the surface coating. Moreover, according to the invention, it is also possible in this way for the flow resistance of the air flowing through the air purification device to be kept relatively low.

According to the invention, it is also preferable that the air purification device has a base element and a cover element, the reaction surface element being integrally connected to the base element or to the cover element, particularly in the form of surface-coated rod-shaped elements protruding into the air conduction volume. In this way it is likewise possible to ensure a particularly well-defined spatial arrangement of the material of the surface coating, which arrangement also remains substantially unchanged during the lifetime of the air purification device. The lighting of the surface coating can in this way be made particularly well-defined and efficient. Moreover, according to the invention, it is also possible in this way for the flow resistance of the air flowing through the air purification device to be kept relatively low. Moreover, by means of the defined arrangement of the surface-coated rod-shaped elements protruding into the air conduction volume, it is also advantageously possible for the flow resistance to remain substantially the same, or to change in a relatively well-defined manner, during the period of use of the air purification device.

According to the invention, it is preferable that the air conduction volume bends at least twice by more than 90° between air inlet and air outlet or that the air conduction volume is designed in a spiral shape between air inlet and air outlet. In this way, particularly good air purification can be achieved in a small space.

It is particularly preferable if the air purification device is integrated in a vehicle bodywork, particularly in the roof area of the vehicle bodywork, in such a way that a part of the vehicle bodywork is provided as a surface-coated wall of the air conduction volume. For example, in an advantageous manner, the space between a roof liner and the vehicle bodywork can be efficiently utilized in this way.

It is also preferable that the air purification device is integrated in a vehicle component, particularly in a roof liner, in such a way that a part of the vehicle component is provided as a surface-coated wall of the air conduction volume. In this way, the space between a roof liner and the vehicle bodywork can likewise be efficiently utilized, but without the need for changes to the bodywork.

The present invention also relates to a vehicle component, in particular an interior trim component, with an integrated air purification device according to the invention, which vehicle component is a roof liner or a rear parcel shelf or a central console or a door lining or an A-pillar lining or a B-pillar lining or a C-pillar lining or an instrument panel.

The invention further relates to the use of a vehicle bodywork or of a part thereof, or of a vehicle component or of a part thereof, as a wall of an air purification device according to the invention.

DRAWINGS

Illustrative embodiments of the invention are shown in the drawing.

FIG. 1 shows a first illustrative embodiment of the air purification system 10 according to the invention or of the air purification device 10 according to the invention.

FIG. 2 shows a second illustrative embodiment of the air purification system 10 according to the invention or of the air purification device 10 according to the invention.

FIG. 3 shows a third illustrative embodiment of the air purification system 10 according to the invention or of the air purification device 10 according to the invention.

FIG. 4 shows a fourth illustrative embodiment of the air purification system 10 according to the invention or of the air purification device 10 according to the invention.

FIG. 5 shows a fifth illustrative embodiment of the air purification system 10 according to the invention or of the air purification device 10 according to the invention.

Figure 6:
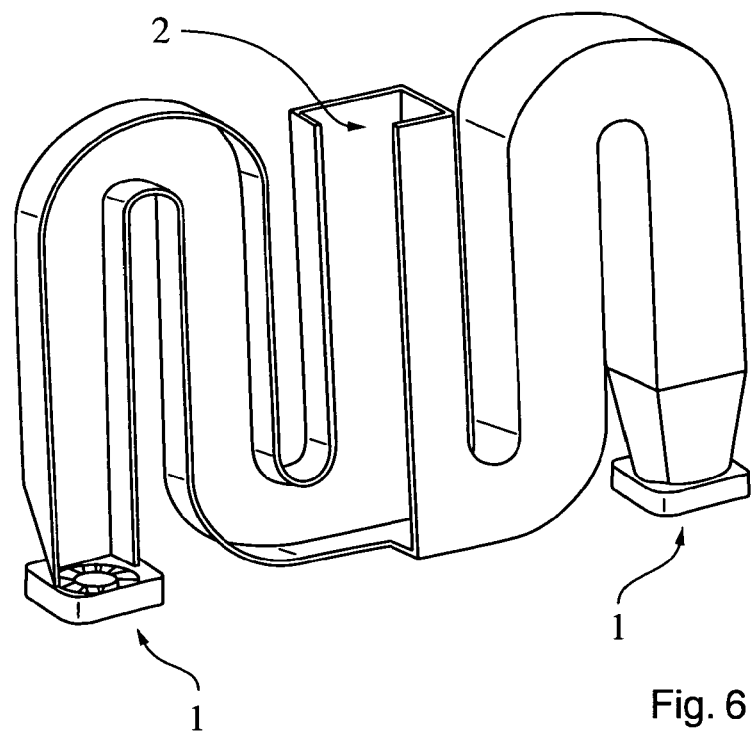
Figure 7:
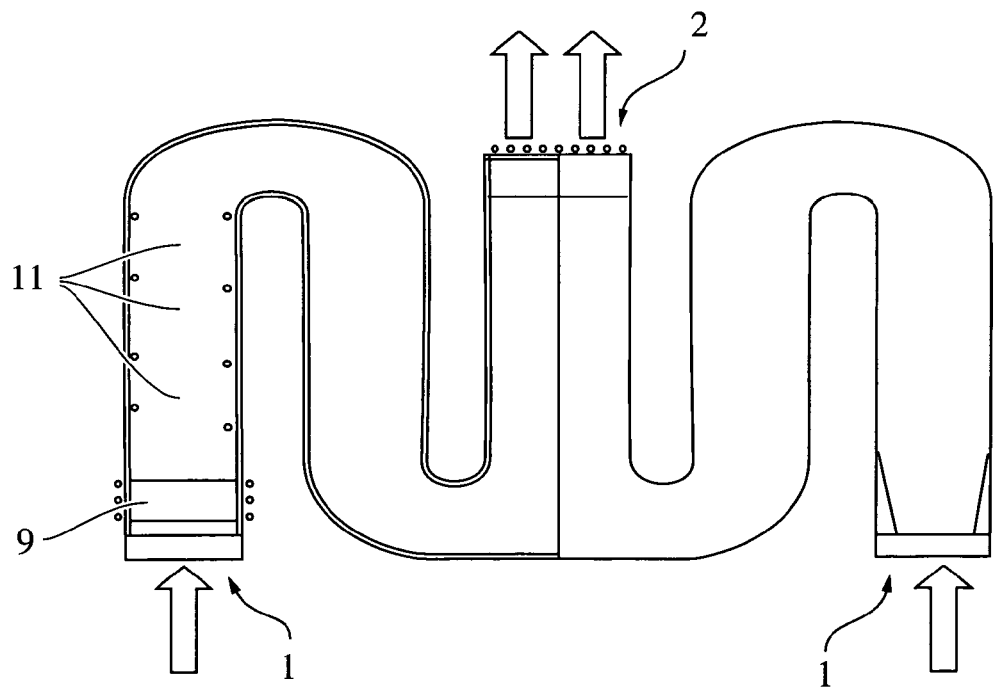

FIGS. 6 and 7 show a sixth illustrative embodiment of the air purification system 10 according to the invention or of the air purification device 10 according to the invention.

Figure 8:
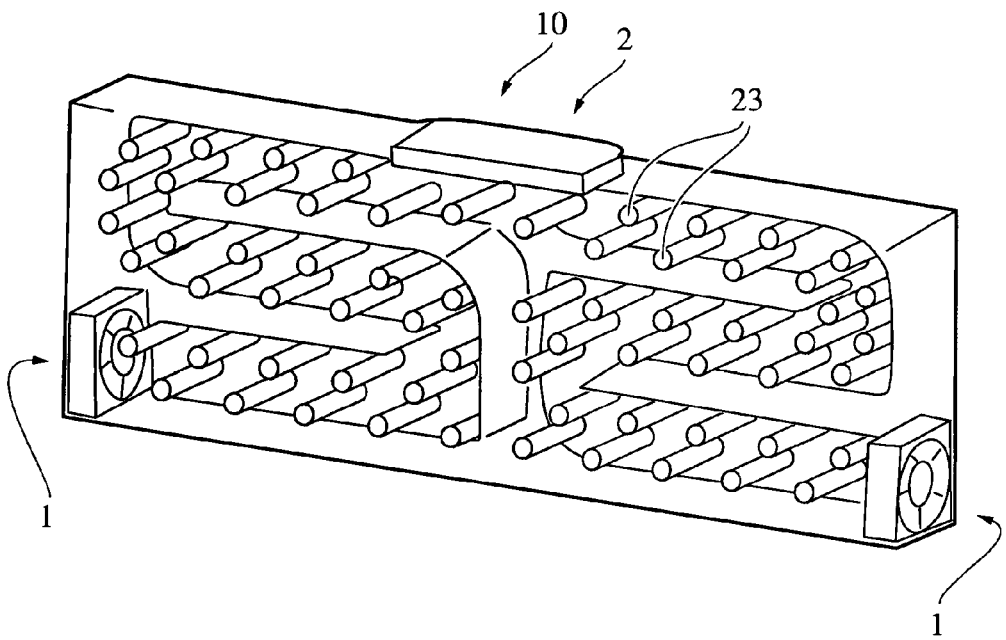
Figure 9:
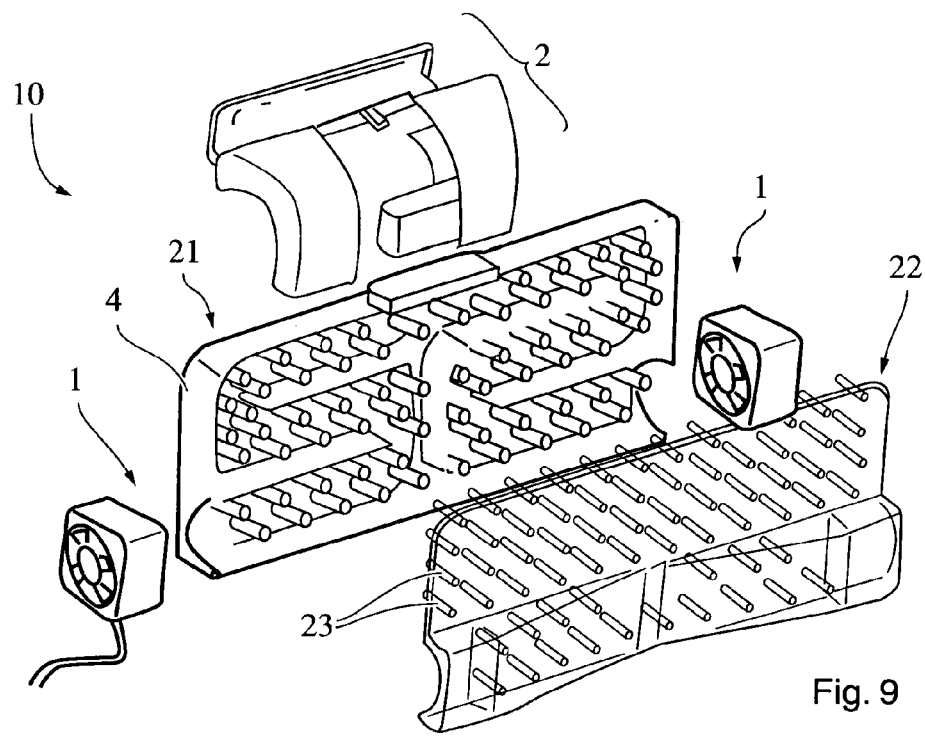

FIGS. 8 and 9 show a seventh illustrative embodiment of the air purification system 10 according to the invention or of the air purification device 10 according to the invention.

Figure 10:
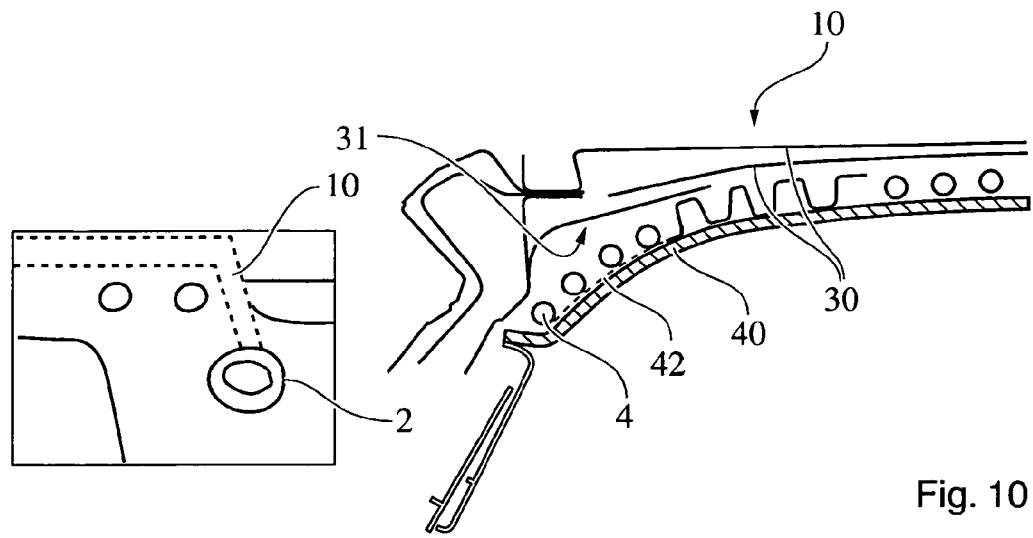

FIG. 10 shows an eighth illustrative embodiment of the air purification system 10 according to the invention or of the air purification device 10 according to the invention.

Figure 11:
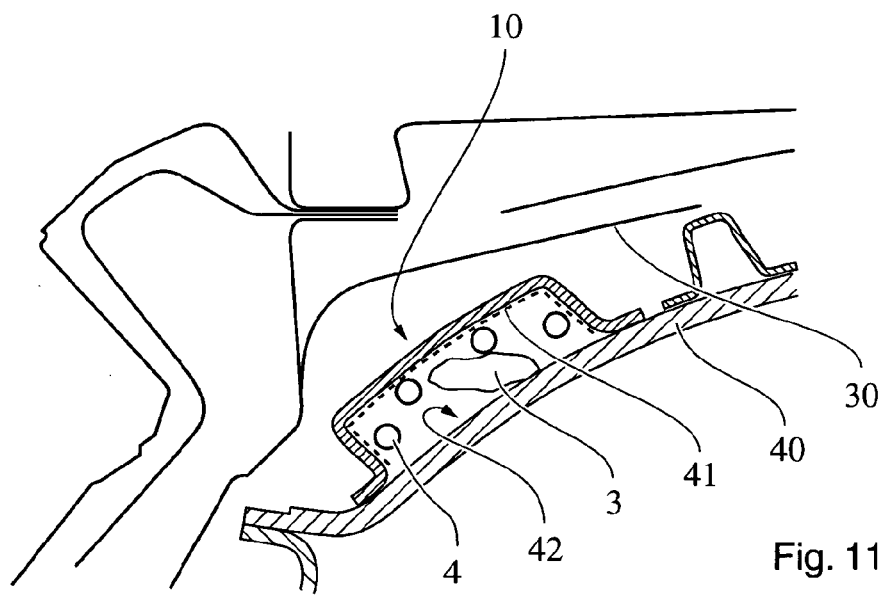

FIG. 11 shows a ninth illustrative embodiment of the air purification system 10 according to the invention or of the air purification device 10 according to the invention.

Figure 12:
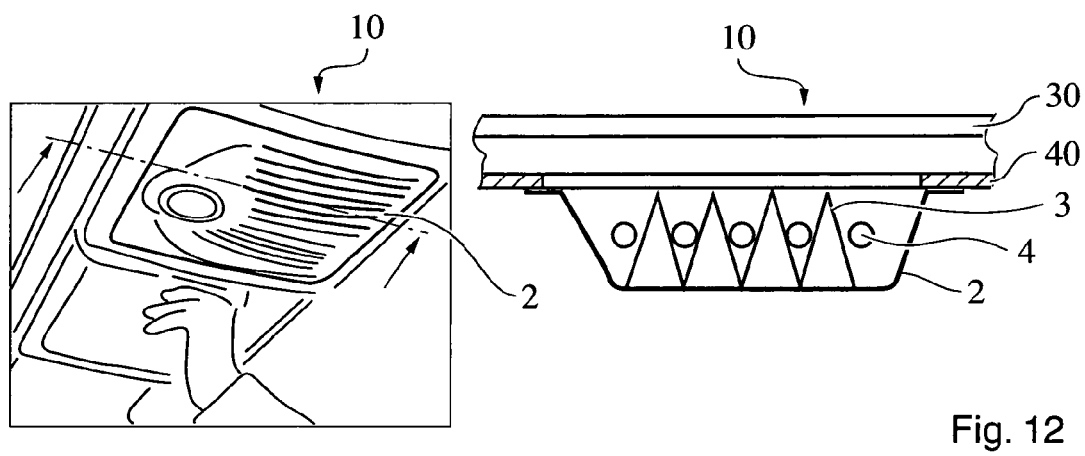

FIG. 12 shows a tenth illustrative embodiment of the air purification system 10 according to the invention or of the air purification device 10 according to the invention.

DETAILED DESCRIPTION

In all of the illustrative embodiments, the air purification device 10 or the air purification system 10 comprises an air inlet 1 and an air outlet 2. Moreover, the air purification device 10 or the air purification system 10 has a housing 5, a light source 4 or a plurality of light sources 4, and a reaction surface element 3 or a plurality of reaction surface elements 3. In the first to fifth illustrative embodiments, the reaction surface element 3 is provided in particular as a lattice or wire mesh provided with a catalytic material (as surface coating). The catalytic material is designed in particular as a titanium dioxide material or comprises titanium dioxide, for example as a nano-structured catalytic material (nano-titanium dioxide). In the first to tenth illustrative embodiments, the light source 4 is provided in the form of a light source 4 that generates ultraviolet radiation (UV radiation), in particular a light source 4 that generates UV-A radiation, particularly in the form of a UV-A tube and/or in the form of a UV-A light-emitting diode or a plurality of UV-A light-emitting diodes. The use of one of more UV-A tubes is especially preferred in particular in the first, second and fifth illustrative embodiments. The use of one or more UV-A light-emitting diodes is especially preferred in particular in the third, fourth and sixth to tenth illustrative embodiments. When UV-A light-emitting diodes are used as the light source, it is particularly preferable according to the invention to use UV-A light-guiding films in order to distribute the light. In all of the illustrative embodiments, at least one fan, for example an axial fan, is provided (per separate air conduction volume, or per separate air conduction volume and further air conduction volume), which fan forces or draws the polluted air through the housing. The fan can either be arranged upstream of the housing 5 (in the direction of air flow) or downstream of the housing 5 (in the direction of air flow). The air flowing through the air purification device comes into contact with the reaction surface element 3 or with the coated surface thereof and is purified, in particular on account of the lighting of the surface of the reaction surface elements 3 by the light source 4 or by the light sources 4. A particularly high degree of efficiency of air purification is achieved here by virtue of the large surface area of the reaction surface element 3 and the large surface area of the light source 4 or of the large number of light sources 4. As a result of the photocatalytic action of UV-A light and titanium dioxide (in particular nano-titanium dioxide), air pollutants (for example smoke/odors/germs/bacteria) are chemically converted and/or eliminated. The efficiency of the air purification can be further increased, according to the invention, by using nano-zeolite substrates and/or nano-silver substrates as reaction surface element. As an alternative to using a zeolite material and/or a silver substrate material as reaction surface element, provision can be made, according to the invention, that these materials are present as a further catalytic material 9 in a further air conduction volume (separate from the air conduction volume), in which case such a further air conduction volume is preferably arranged in the area of the inlet 1 or in the area of the outlet 2. This alternative embodiment is shown only in FIG. 7.

The design of the reaction surface element 3, of the light source 4 and of the housing 5 differs in the illustrative embodiments.

Figure 1:
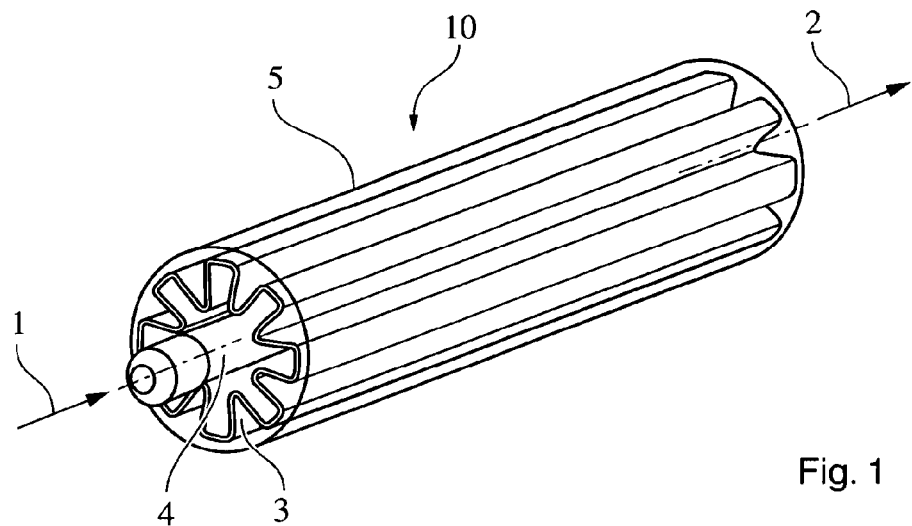
FIGS. 1 to 12 show ten different illustrative embodiments, according to the invention, of the air purification system according to the invention or of the air purification device according to the invention.
Figure 5:
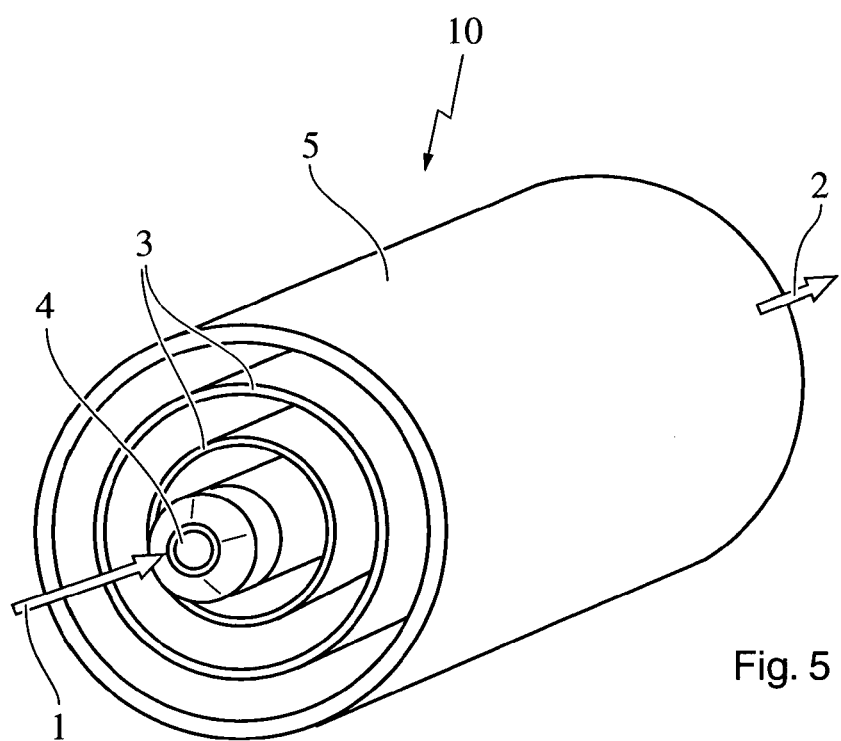

Thus, in the first, second and fifth illustrative embodiments (FIGS. 1, 2 and 5), the housing 5 is tubular or cylindrical at least in sections. The air inlet 1 and the air outlet 2 are provided at the end faces of the tube. The light source 4, particularly as UV-A tube, is arranged in the center of the tube, although it is also possible to provide a light guide system with a common central UV-A light source 4. The reaction surface element 3 is arranged in the area radially between the light source 4 and the housing 5. A fan (not shown), in particular an axial fan, is arranged on the air inlet side. The purified air emerges at the air outlet side. In the first illustrative embodiment (FIG. 1), the cross section of the reaction surface element 3 is in particular star-shaped or meander-shaped. In the second illustrative embodiment (FIG. 2), the reaction surface element 3 is spiral-shaped for example. In the fifth illustrative embodiment (FIG. 5), the reaction surface element 3 has a substantially tubular shape, and in this case two reaction surface elements 3 of different diameter are provided between the light source 4 and the housing.

Figure 2:
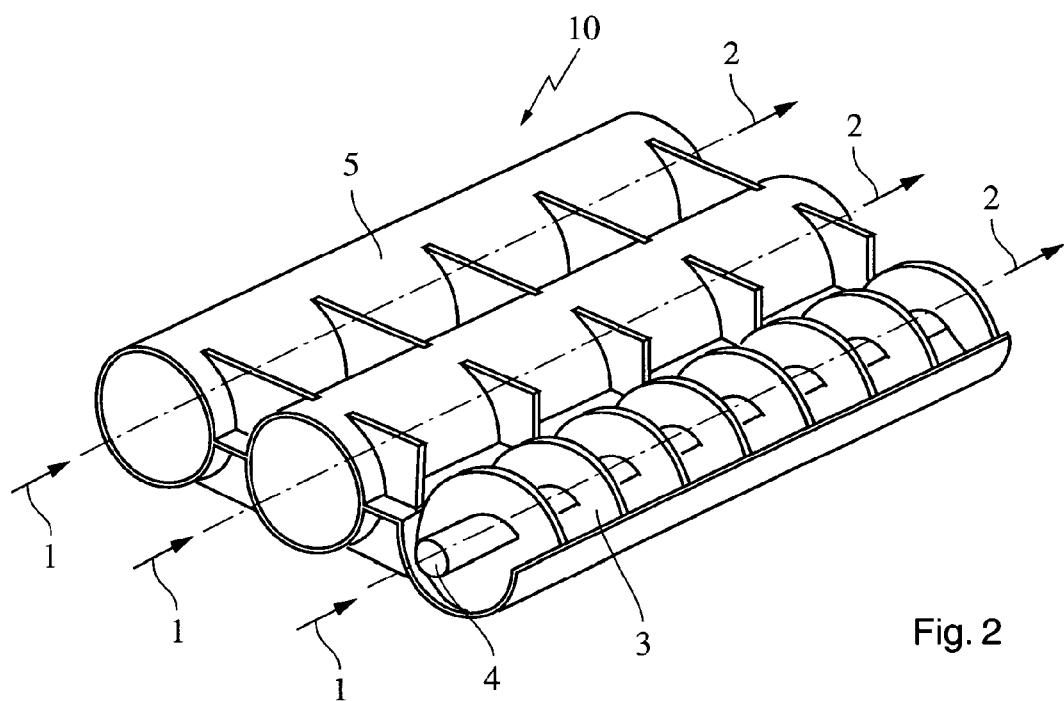

In the first, second and fifth illustrative embodiments (FIGS. 1, 2 and 5), a plurality of tubular or cylindrical sections can also be provided in parallel and/or arranged one behind another. A parallel arrangement is shown in FIG. 2, for example. An arrangement of two tubular or cylindrical sections one behind another can be obtained, for example, if the air outlet side of one tube is coupled to the air inlet side of the other tube and the air first passes through one tube, is then deflected and then passes through the other tube (particularly in the opposite direction). With five tubular or cylindrical sections of this kind, it is possible, for example, for a fan to be provided on the two outer air channels, in which case the inner air channels are coupled to one another in such a way that a central outlet is formed in the middle.

Figure 3:
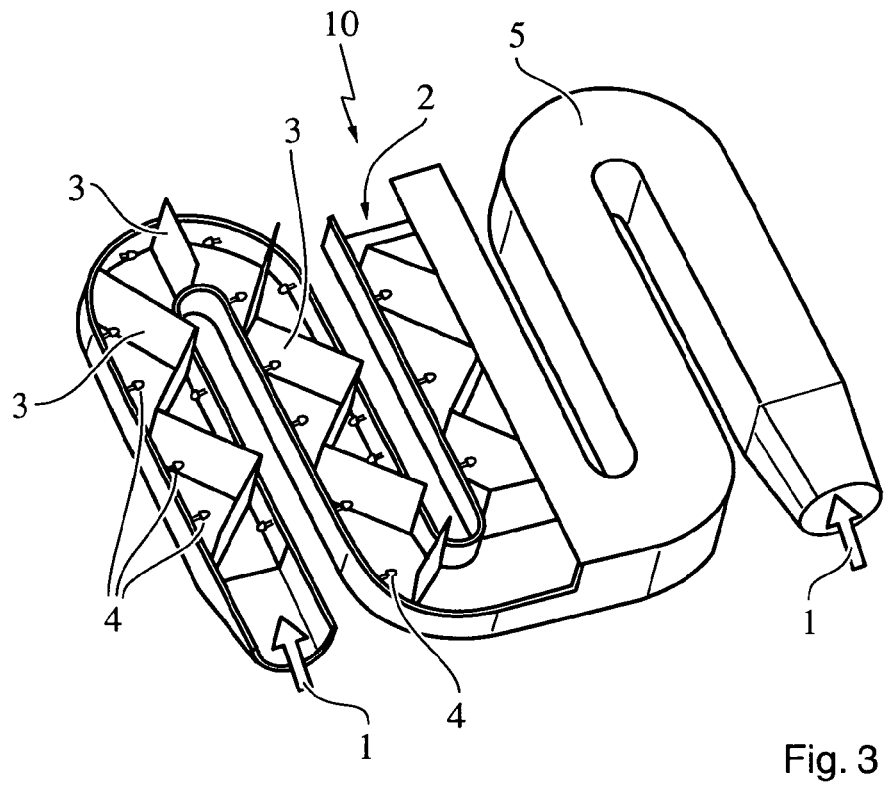
Figure 4:
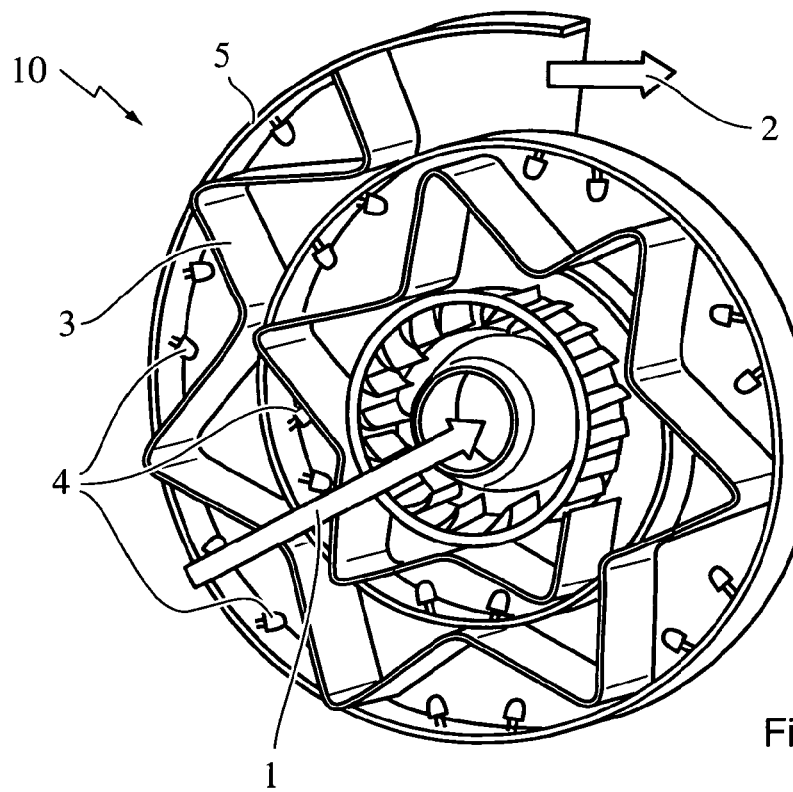

In the third and fourth illustrative embodiments (FIGS. 3 and 4), the reaction surface element 3 is provided mainly in a zigzag shape or meandering shape or like a concertina across the cross section of the air channel of the housing 5. In the third illustrative embodiment (FIG. 3), the air channel of the housing is itself provided meandering with a first limb, a turn-round (of the air conduction volume through approximately 180°), a second limb, another turn-round (of the air conduction volume through approximately 180°), and a third limb. In the fourth illustrative embodiment (FIG. 4), the air channel of the housing is provided in a spiral shape. A radial fan in particular is provided at the center of the spiral, which represents the air inlet 1.

In the sixth and seventh illustrative embodiments (FIGS. 6 to 9), the air channel of the housing is itself once again provided meandering with a first limb, a turn-round (of the air conduction volume through approximately 180°), a second limb, another turn-round (of the air conduction volume through approximately 180°), and a third limb.

In the sixth illustrative embodiment (FIGS. 6 and 7), the reaction surface element 3 is provided as a bulk material 11 (or a multiplicity of reaction surface elements 3 are provided). For example, the reaction surface elements 3 are provided in the form of a plurality of short glass tubes (or glass tube sections) which are provided with a surface coating and are distributed across substantially the entire space of the air conduction volume. This is indicated in FIG. 7. As an alternative to the use of glass tubes, it is possible to use surface-coated glass balls. Moreover, it is also possible, according to the invention, to use a mixture of surface-coated glass tubes and glass balls. In all cases of the sixth illustrative embodiment (FIGS. 6 and 7), the reaction surface elements 3 are distributed across substantially the entire space of the air conduction volume. As an alternative or in addition to surface-coated glass elements (glass tube sections or glass balls), it is also possible to use transparent or opaque plastic tube sections (small plastic tubes) or other spherical and transparent or opaque plastic structures as reaction surface elements 3.

As reaction surface element 3 in the seventh illustrative embodiment (FIGS. 8 and 9), provision is made that the air purification device 10 has a base element 21 and a cover element 22, the reaction surface element 3 being integrally connected to the base element 21 or to the cover element 22, particularly in the form of surface-coated rod-shaped elements 23 protruding into the air conduction volume. Of course, provision can also be made, according to the invention, that rod-shaped elements 23 are designed extending both from the base element 21 and also from the cover element 22. Moreover, in the seventh illustrative embodiment (FIGS. 8 and 9), it is advantageously possible, according to the invention, that almost the entire inner surface of the air purification device 10 is surface-coated and thus acts as reaction surface element 3, in which case, however, sufficient space has to be provided in which to arrange the light source 4 or the plurality of light sources 4.

According to the eighth illustrative embodiment (FIG. 10), provision is made that the air purification device 10 is integrated in a vehicle bodywork 30, particularly in the roof area of the vehicle bodywork 30, in such a way that a part of the vehicle bodywork 30 is provided as a surface-coated wall 31 of the air conduction volume. This is shown schematically in FIG. 10 using the example of a roof area of the vehicle bodywork and of a roof liner facing the interior of the vehicle as an example of a vehicle component 40. The left-hand part of FIG. 10 shows a view of the roof liner as it may appear to an occupant of the vehicle. The dashed line indicates an air conduction channel or an air purification device 10 on the side of the roof liner 40 directed away from the occupant of the vehicle, which roof liner 40 opens into an air outlet 2. The right-hand part of FIG. 10 shows a schematic and sectional view through such an air conduction channel or such an air purification device 10. A bodywork wall 31 of the air conduction channel or of the air purification device 10 is provided with a surface coating and contributes to the air purification as air flows through the air channel. Light sources 4 are provided on the side of the vehicle component 40 directed away from the occupant of the vehicle. Alternatively or in addition in the eighth illustrative embodiment (FIG. 10), provision can also be made, according to the invention, that the side 42 of the vehicle component 40 directed toward the bodywork is additionally provided with a surface coating. In the eighth illustrative embodiment (FIG. 10), it is particularly advantageous that the installation space between the vehicle component 40 (for example a roof liner or some other lining inside a vehicle) and the bodywork 30 can be used particularly efficiently for air purification. Alternatively or in addition, provision can also be made that the vehicle component 40 is designed to be air-permeable at least in some areas, in such a way that no outwardly visible air outlet openings can be seen, and instead the air flows through the material of the vehicle component. If the side 42 of the vehicle component 40 directed toward the bodywork 30 is surface-coated, an air purification effect can additionally be achieved.

According to the ninth illustrative embodiment (FIG. 11), provision is made that the air purification device 10 is integrated in a vehicle component 40, particularly in a roof liner, in such a way that a part of the vehicle component 40 is provided as a surface-coated wall 41 of the air conduction volume. In the example shown in FIG. 11, a cross section through such an air conduction channel or such an air purification device 10 is shown schematically. A surface-coated wall 41 of the air purification device 10 is part of the vehicle component 40 (i.e. for example of a lining element such as a roof liner) and contributes to the air purification as air flows through the air channel. Light sources 4 are provided on the side of the vehicle component 40 directed away from the occupant of the vehicle. Alternatively or in addition in the ninth illustrative embodiment (FIG. 11), provision can also be made, according to the invention, that the side 42 of the vehicle component 40 directed toward the surface-coated wall 41 is additionally provided with a surface coating. In the ninth illustrative embodiment (FIG. 11), it is particularly advantageous that the installation space between the vehicle component 40 (for example a roof liner or some other lining inside a vehicle) and the bodywork 30 can be used particularly efficiently for air purification. Alternatively or in addition, provision can also be made that the vehicle component 40 is designed to be air-permeable at least in some areas, in such a way that no outwardly visible air outlet openings can be seen, and instead the air flows through the material of the vehicle component. If the side 42 of the vehicle component 40 directed toward the surface-coated wall 41 is surface-coated, an air purification effect can additionally be achieved.

If, in the eighth and ninth illustrative embodiments (FIG. 11), only one wall or several walls of the air purification device 10 are surface-coated, the reaction surface element 3 is then formed by these walls. Alternatively or in addition to such a design however, it is also possible, in the eighth and ninth illustrative embodiments (FIGS. 10 and 11), that reaction surface elements 3 either in the form of surface-coated lattices or fabrics or else in the form of surface-coated bulk material are introduced into the air purification device 10 in order to thereby increase the air purification effect still further.

According to the tenth illustrative embodiment (FIG. 12), provision is made that an air purification device 10 according to the invention, and as per the first to seventh illustrative embodiments (FIGS. 1 to 9), is installed in a vehicle component 40, for example in the area of the roof liner. Thus, for example, the left-hand side of FIG. 12 shows a schematic and perspective view of such an air purification device 10 integrated in the roof liner, in which view an air outlet 2 can be seen. The right-hand side of FIG. 12 shows a schematic cross section of the air purification device 10, illustrating the vehicle component 40, the bodywork 30, the outlet 2, the light source 4 and a reaction surface element 3.

As an alternative to arranging the air purification device 10 in the area of the roof liner, provision can also advantageously be made, according to the invention, to arrange the air purification device 10 in the area of the rear parcel shelf and/or in the area of a central console of the vehicle and/or in the area of a door lining of the vehicle and/or in the area of an A-pillar lining of the vehicle and/or in the area of a B-pillar lining of the vehicle and/or in the area of a C-pillar lining of the vehicle.

LIST OF REFERENCE SYMBOLS

1 air inlet
2 air outlet
3 reaction surface element
4 light source
5 housing
9 further catalytic material
10 air purification system/air purification device
21 base element
22 cover element
23 rod-shaped elements
30 vehicle bodywork
31 surface-coated wall
40 vehicle component
41 surface-coated wall of the air conduction volume
42 side directed toward the bodywork

The invention claimed is:

1. An air purification device for a vehicle, comprising an air inlet, an air outlet, an air conduction volume between the air inlet and the air outlet, at least one reaction surface element in the air conduction volume, and at least one light source configured to emit ultraviolet light in the air conduction volume, wherein a surface of the at least one reaction surface element comprises a catalytic material, and wherein the at least one reaction surface element is arranged substantially in the entire air conduction volume or occupies at least 50% of an inner surface of the air purification device;

wherein the at least one reaction surface element is formed from a substantially flat sheet of material, the at least one reaction surface element extends through at least a portion of the air conduction volume along an airflow direction between the air inlet and the air outlet such that a first end of the substantially flat sheet of material is positioned downstream from a second end of the substantially flat sheet of material relative to the airflow direction, the substantially flat sheet of material zigzags or meanders between opposing walls of the air conduction volume to form a plurality of reaction surface element segments, the plurality of reaction surface element segments are arranged in succession along the airflow direction between the first end of the substantially flat sheet of material and the second end of the substantially flat sheet of material, and each of the plurality of reaction surface element segments extends across at least a portion of a cross-section of the air conduction volume between the opposing walls.

2. The air purification device as claimed in claim 1, wherein the at least one reaction surface element is arranged in at least 60% of the air conduction volume.

3. The air purification device as claimed in claim 1, wherein the catalytic material contains titanium dioxide.

4. The air purification device as claimed in claim 1, wherein the at least one light source comprises a plurality of light-emitting diodes.

5. The air purification device as claimed in claim 1, wherein the air purification device is integrated in a roof area of the vehicle, or the air purification device is integrated in a roof liner of the vehicle.

6. The air purification device as claimed in claim 5, wherein the air purification device is integrated in the roof area or the roof liner in such a way that a part of the roof area or the roof liner is provided as a surface-coated wall of the air conduction volume.

7. An air purification device for a vehicle, comprising an air inlet, an air outlet, an air conduction volume between the air inlet and the air outlet, at least one reaction surface element in the air conduction volume, and at least one light source configured to emit ultraviolet light in the air conduction volume, wherein a surface of the at least one reaction surface element comprises a catalytic material, and wherein the at least one reaction surface element is arranged substantially in the entire air conduction volume or occupies at least 50% of an inner surface of the air purification device;
wherein the at least one reaction surface element is formed from a substantially flat sheet of material, the at least one reaction surface element extends through at least a portion of the air conduction volume along an airflow direction between the air inlet and the air outlet such that a first end of the substantially flat sheet of material is positioned downstream from a second end of the substantially flat sheet of material relative to the airflow direction, the substantially flat sheet of material zigzags or meanders between opposing walls of the air conduction volume to form a plurality of reaction surface element segments, the plurality of reaction surface element segments are arranged in succession along the airflow direction between the first end of the substantially flat sheet of material and the second end of the substantially flat sheet of material, and each of the plurality of reaction surface element segments extends across at least a portion of a cross-section of the air conduction volume between the opposing walls;
wherein the air conduction volume bends at least twice by more than 90° between the air inlet and the air outlet.

8. The air purification device as claimed in claim 7, wherein the catalytic material contains titanium dioxide.

9. The air purification device as claimed in claim 7, wherein the at least one light source comprises a plurality of light-emitting diodes.

10. The air purification device as claimed in claim 7, wherein the air purification device is integrated in a roof area of the vehicle, or the air purification device is integrated in a roof liner of the vehicle.

11. The air purification device as claimed in claim 10, wherein the air purification device is integrated in the roof area or the roof liner in such a way that a part of the roof area or the roof liner is provided as a surface-coated wall of the air conduction volume.

12. An air purification device for a vehicle, comprising an air inlet, an air outlet, an air conduction volume between the air inlet and the air outlet, at least one reaction surface element in the air conduction volume, and at least one light source configured to emit ultraviolet light in the air conduction volume, wherein a surface of the at least one reaction surface element comprises a catalytic material, and wherein the at least one reaction surface element is arranged substantially in the entire air conduction volume or occupies at least 50% of an inner surface of the air purification device;
wherein the at least one reaction surface element is formed from a substantially flat sheet of material, the at least one reaction surface element extends through at least a portion of the air conduction volume along an airflow direction between the air inlet and the air outlet such that a first end of the substantially flat sheet of material is positioned downstream from a second end of the substantially flat sheet of material relative to the airflow direction, the substantially flat sheet of material zigzags or meanders between opposing walls of the air conduction volume to form a plurality of reaction surface element segments, the plurality of reaction surface element segments are arranged in succession along the airflow direction between the first end of the substantially flat sheet of material and the second end of the substantially flat sheet of material, and each of the plurality of reaction surface element segments extends across at least a portion of a cross-section of the air conduction volume between the opposing walls;
wherein the air purification device has an additional air conduction volume, the additional air conduction volume having a zeolite material and/or a silver substrate material as an additional catalytic material.

13. The air purification device as claimed in claim 12, wherein the at least one reaction surface element is arranged in at least 60% of the air conduction volume.

14. The air purification device as claimed in claim 12, wherein the catalytic material contains titanium dioxide.

15. The air purification device as claimed in claim 12, wherein the air conduction volume bends at least twice by more than 90° between the air inlet and the air outlet.

16. The air purification device as claimed in claim 12, wherein the air conduction volume comprises a spiral shape between the air inlet and the air outlet.

17. The air purification device as claimed in claim 12, wherein the at least one light source comprises a plurality of light-emitting diodes.

18. The air purification device as claimed in claim 12, wherein the at least one reaction surface element is arranged in at least 80% of the air conduction volume.

19. The air purification device as claimed in claim 12, wherein the air purification device is integrated in a roof area of the vehicle, or the air purification device is integrated in a roof liner of the vehicle.

20. The air purification device as claimed in claim 19, wherein the air purification device is integrated in the roof area or the roof liner in such a way that a part of the roof area or the roof liner is provided as a surface-coated wall of the air conduction volume.

* * * * *